(12) United States Patent
Lopez (10) Patent No.: US 11,103,712 B2
(45) Date of Patent: Aug. 31, 2021

(54) CONNECTOR ASSEMBLIES WITH NOVEL SPACERS FOR ELECTRICAL STIMULATION SYSTEMS AND METHODS OF MAKING AND USING SAME

(71) Applicant: Boston Scientific Neuromodulation Corporation, Valencia, CA (US)

(72) Inventor: Thomas Paul Lopez, Sunland, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 309 days.

(21) Appl. No.: 16/247,293

(22) Filed: Jan. 14, 2019

(65) Prior Publication Data

US 2019/0217103 A1   Jul. 18, 2019

Related U.S. Application Data

(60) Provisional application No. 62/617,990, filed on Jan. 16, 2018.

(51) Int. Cl.
*A61N 1/375* (2006.01)
*A61N 1/05* (2006.01)
(Continued)

(52) U.S. Cl.
CPC ......... *A61N 1/3752* (2013.01); *A61N 1/0553* (2013.01); *A61N 1/36071* (2013.01);
(Continued)

(58) Field of Classification Search
CPC ............... A61N 1/3752; A61N 1/0553; A61N 1/36071; A61N 1/0534
See application file for complete search history.

(56) References Cited

U.S. PATENT DOCUMENTS 3,222,471 A   12/1965 Steinkamp
3,601,747 A   8/1971 Prall et al.
(Continued)

FOREIGN PATENT DOCUMENTS

EP   0580928 A1   2/1994
EP   0650694 B1   7/1998
(Continued)

*Primary Examiner* — Joseph M Dietrich
(74) *Attorney, Agent, or Firm* — Branch Partners PLLC; Bruce E. Black (57) ABSTRACT

A connector assembly includes an elongated connector housing having a first end, a second end, and a length, the connector housing defining a port at the second end of the connector housing for receiving a proximal end of a lead or lead extension; a lead lumen that extends from the port into the connector housing; connector contacts axially spaced-apart and disposed along the lead lumen for coupling to terminals along a proximal end of a lead or lead extension; and non-conductive spacers disposed between adjacent connector contacts. Each of the spacers includes a first radial sidewall, a second radial sidewall, and an intermediate region extending between, and connecting, the first and second radial sidewalls. The first and second radial sidewalls and intermediate region define boundaries of an open circumferential space opposite the lead lumen with respect to the intermediate region.

20 Claims, 7 Drawing Sheets (51) Int. Cl.
   *A61N 1/36*  (2006.01)
   *H01R 13/52*  (2006.01)
   *H01R 24/58*  (2011.01)

(52) U.S. Cl.
   CPC ........ *A61N 1/0534* (2013.01); *H01R 13/5224* (2013.01); *H01R 24/58* (2013.01); *H01R 2201/12* (2013.01)

(56) References Cited

U.S. PATENT DOCUMENTS

| | | |
|---|---|---|
| 3,718,142 A | 2/1973 | Mulier |
| 3,757,789 A | 9/1973 | Shanker |
| 3,771,106 A | 11/1973 | Matsumoto et al. |
| 3,908,668 A | 9/1975 | Bolduc |
| 3,951,154 A | 4/1976 | Hartlaub |
| 3,990,727 A | 11/1976 | Gallagher |
| 4,003,616 A | 1/1977 | Springer |
| 4,112,953 A | 9/1978 | Shanker et al. |
| 4,142,532 A | 3/1979 | Ware |
| 4,180,078 A | 12/1979 | Anderson |
| 4,245,642 A | 1/1981 | Skubitz et al. |
| 4,259,962 A | 4/1981 | Peers-Trevarton |
| 4,310,001 A | 1/1982 | Comben |
| 4,364,625 A | 12/1982 | Baker et al. |
| 4,367,907 A | 1/1983 | Buck |
| 4,411,276 A | 10/1983 | Dickhudt et al. |
| 4,411,277 A | 10/1983 | Dickhudt |
| 4,461,194 A | 7/1984 | Moore |
| 4,466,441 A | 8/1984 | Skubitz et al. |
| 4,516,820 A | 5/1985 | Kuzma |
| RE31,990 E | 9/1985 | Sluetz et al. |
| 4,540,236 A | 9/1985 | Peers-Trevarton |
| 4,602,624 A | 7/1986 | Naples et al. |
| 4,603,696 A | 8/1986 | Cross, Jr. et al. |
| 4,614,395 A | 9/1986 | Peers-Trevarton |
| 4,630,611 A | 12/1986 | King |
| 4,695,116 A | 9/1987 | Bailey et al. |
| 4,695,117 A | 9/1987 | Kysiak |
| 4,712,557 A | 12/1987 | Harris |
| 4,715,380 A | 12/1987 | Harris |
| 4,744,370 A | 5/1988 | Harris |
| 4,784,141 A | 11/1988 | Peers-Trevarton |
| 4,832,032 A | 5/1989 | Schneider |
| 4,840,580 A | 6/1989 | Saell et al. |
| 4,850,359 A | 7/1989 | Putz |
| 4,860,750 A | 8/1989 | Frey et al. |
| 4,867,708 A | 9/1989 | Iizuka |
| 4,869,255 A | 9/1989 | Putz |
| 4,898,173 A | 2/1990 | Daglow et al. |
| 4,899,753 A | 2/1990 | Inoue et al. |
| 4,951,687 A | 8/1990 | Ufford et al. |
| 4,995,389 A | 2/1991 | Harris |
| 5,000,177 A | 3/1991 | Hoffman et al. |
| 5,000,194 A | 3/1991 | van den Honert et al. |
| 5,007,435 A | 4/1991 | Doan et al. |
| 5,007,864 A | 4/1991 | Stutz, Jr. |
| 5,070,605 A | 12/1991 | Daglow et al. |
| 5,082,453 A | 1/1992 | Stutz, Jr. |
| 5,086,773 A | 2/1992 | Ware |
| 5,135,001 A | 8/1992 | Sinofsky et al. |
| 5,193,539 A | 3/1993 | Schulman et al. |
| 5,193,540 A | 3/1993 | Schulman et al. |
| 5,201,865 A | 4/1993 | Kuehn |
| 5,241,957 A | 9/1993 | Camps et al. |
| 5,252,090 A | 10/1993 | Giurtino et al. |
| 5,261,395 A | 11/1993 | Oleen et al. |
| 5,312,439 A | 5/1994 | Loeb |
| 5,324,312 A | 6/1994 | Stokes et al. |
| 5,330,521 A | 7/1994 | Cohen |
| 5,336,246 A | 8/1994 | Dantanarayana |
| 5,348,481 A | 9/1994 | Ortiz |
| 5,354,326 A | 10/1994 | Comben et al. |
| 5,358,514 A | 10/1994 | Schulman et al. |
| 5,368,496 A | 11/1994 | Ranalletta et al. |
| 5,374,279 A | 12/1994 | Duffin, Jr. et al. |
| 5,374,285 A | 12/1994 | Vaiani et al. |
| 5,383,913 A | 1/1995 | Schiff |
| 5,413,595 A | 5/1995 | Stutz, Jr. |
| 5,433,734 A | 7/1995 | Stokes et al. |
| 5,435,731 A | 7/1995 | Kang |
| 5,458,629 A | 10/1995 | Baudino et al. |
| 5,486,202 A | 1/1996 | Bradshaw |
| 5,489,225 A | 2/1996 | Julian |
| 5,509,928 A | 4/1996 | Acken |
| 5,522,874 A | 6/1996 | Gates |
| 5,534,019 A | 7/1996 | Paspa |
| 5,545,188 A | 8/1996 | Bradshaw et al. |
| 5,545,189 A | 8/1996 | Fayram |
| 5,582,180 A | 8/1996 | Manset et al. |
| 5,560,358 A | 10/1996 | Arnold et al. |
| 5,679,026 A | 10/1997 | Fain et al. |
| 5,683,433 A | 11/1997 | Carson |
| 5,711,316 A | 1/1998 | Elsberry et al. |
| 5,713,922 A | 2/1998 | King |
| 5,720,631 A | 2/1998 | Carson et al. |
| 5,730,628 A | 3/1998 | Hawkins |
| 5,755,743 A | 5/1998 | Volz et al. |
| 5,766,042 A | 6/1998 | Ries et al. |
| 5,782,892 A | 7/1998 | Castle et al. |
| 5,796,044 A | 8/1998 | Cobian et al. |
| 5,800,350 A | 9/1998 | Coppleson et al. |
| 5,800,495 A | 9/1998 | Machek et al. |
| 5,807,144 A | 9/1998 | Sivard |
| 5,837,006 A | 11/1998 | Ocel et al. |
| 5,843,141 A | 12/1998 | Bischoff et al. |
| 5,843,148 A | 12/1998 | Gijsbers et al. |
| 5,906,634 A | 5/1999 | Flynn et al. |
| 5,931,861 A | 8/1999 | Werner et al. |
| 5,938,688 A | 8/1999 | Schiff |
| 5,951,595 A | 9/1999 | Moberg et al. |
| 5,968,082 A | 10/1999 | Heil |
| 5,987,361 A | 11/1999 | Mortimer |
| 5,989,077 A | 11/1999 | Mast et al. |
| 6,006,135 A | 12/1999 | Kast et al. |
| 6,018,684 A | 1/2000 | Bartig et al. |
| 6,038,479 A | 3/2000 | Werner et al. |
| 6,038,481 A | 3/2000 | Werner et al. |
| 6,042,432 A | 3/2000 | Hashazawa et al. |
| 6,051,017 A | 4/2000 | Loeb et al. |
| 6,080,188 A | 6/2000 | Rowley et al. |
| 6,112,120 A | 8/2000 | Correas |
| 6,112,121 A | 8/2000 | Paul et al. |
| 6,125,302 A | 9/2000 | Kuzma |
| 6,134,478 A | 10/2000 | Spehr |
| 6,154,678 A | 11/2000 | Lauro |
| 6,161,047 A | 12/2000 | King et al. |
| 6,162,101 A | 12/2000 | Fischer et al. |
| 6,164,284 A | 12/2000 | Schulman et al. |
| 6,167,311 A | 12/2000 | Rezai |
| 6,167,314 A | 12/2000 | Fischer, Sr. et al. |
| 6,175,710 B1 | 1/2001 | Kamaji et al. |
| 6,181,969 B1 | 1/2001 | Gord |
| 6,185,452 B1 | 2/2001 | Schulman et al. |
| 6,192,278 B1 | 2/2001 | Werner et al. |
| 6,198,969 B1 | 3/2001 | Kuzma |
| 6,208,894 B1 | 3/2001 | Schulman et al. |
| 6,224,450 B1 | 5/2001 | Norton |
| 6,271,094 B1 | 8/2001 | Boyd et al. |
| 6,295,944 B1 | 10/2001 | Lovett |
| 6,319,021 B1 | 11/2001 | Billman |
| 6,321,126 B1 | 11/2001 | Kuzma |
| 6,322,559 B1 | 11/2001 | Daulton et al. |
| 6,343,233 B1 | 1/2002 | Werner et al. |
| 6,364,278 B1 | 4/2002 | Lin et al. |
| 6,370,434 B1 | 4/2002 | Zhang et al. |
| 6,391,985 B1 | 5/2002 | Goode et al. |
| 6,397,108 B1 | 5/2002 | Camps et al. |
| 6,415,168 B1 | 7/2002 | Putz |
| 6,428,336 B1 | 8/2002 | Akerfeldt |
| 6,428,368 B1 | 8/2002 | Hawkins et al. |
| 6,430,442 B1 | 8/2002 | Peters et al. |
| 6,466,824 B1 | 10/2002 | Struble |
| 6,473,654 B1 | 10/2002 | Chinn |

(56) References Cited

U.S. PATENT DOCUMENTS

| | | |
|---|---|---|
| 6,498,952 B2 | 12/2002 | Imani et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,604,283 B1 | 8/2003 | Kuzma |
| 6,605,094 B1 | 8/2003 | Mann et al. |
| 6,609,029 B1 | 8/2003 | Mann et al. |
| 6,609,032 B1 | 8/2003 | Woods et al. |
| 6,654,641 B1 | 11/2003 | Froberg |
| 6,662,035 B2 | 12/2003 | Sochor |
| 6,663,570 B2 | 12/2003 | Mott |
| 6,671,534 B2 | 12/2003 | Putz |
| 6,671,553 B1 | 12/2003 | Helland et al. |
| 6,678,564 B2 | 1/2004 | Ketterl et al. |
| 6,725,096 B2 | 4/2004 | Chinn et al. |
| 6,741,892 B1 | 5/2004 | Meadows et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,913,478 B2 | 7/2005 | Lamrey |
| 6,921,295 B2 | 7/2005 | Sommer et al. |
| 6,968,235 B2 | 11/2005 | Belden et al. |
| 6,980,863 B2 | 12/2005 | van Venrooij et al. |
| 7,027,852 B2 | 4/2006 | Helland |
| 7,047,084 B2 | 5/2006 | Erickson et al. |
| 7,058,452 B2 | 6/2006 | Dahberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Brase et al. |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,512,446 B2 | 3/2009 | Honeck |
| 7,516,447 B2 | 3/2009 | Drew |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,590,451 B2 | 9/2009 | Tronnes et al. |
| 7,650,184 B2 | 1/2010 | Walter |
| 7,668,601 B2 | 2/2010 | Hegland et al. |
| 7,672,734 B2 | 3/2010 | Anderson et al. |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,803,021 B1 | 9/2010 | Brase |
| 7,809,446 B2 | 10/2010 | Meadows |
| 7,822,477 B2 | 10/2010 | Rey et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B1 | 3/2012 | Daglow et al. |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kast et al. |
| 8,527,054 B2 | 9/2013 | North |
| 8,583,237 B2 | 11/2013 | Bedenbaugh |
| 8,600,507 B2 | 12/2013 | Brass et al. |
| 8,682,439 B2 | 3/2014 | DeRohan et al. |
| 8,688,235 B1 | 4/2014 | Pianca et al. |
| 8,784,143 B2 | 7/2014 | Edgell et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,234,591 B2 | 1/2016 | Dilmaghanian et al. |
| 9,270,070 B2 | 2/2016 | Pianca |
| 9,289,596 B2 | 3/2016 | Leven |
| 9,352,147 B2 | 5/2016 | Nguyen-stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,618 B2 | 11/2016 | Stetson et al. |
| 9,498,620 B2 | 11/2016 | Romero et al. |
| 9,504,839 B2 | 11/2016 | Leven |
| 9,604,068 B2 | 3/2017 | Malinowski |
| 9,656,093 B2 | 5/2017 | Villarta et al. |
| 9,770,598 B2 | 9/2017 | Malinowski et al. |
| 9,855,413 B2 | 1/2018 | Vadlamudi et al. |
| 2001/0023368 A1 | 9/2001 | Black et al. |
| 2002/0143376 A1 | 10/2002 | Chinn et al. |
| 2002/0156513 A1 | 10/2002 | Borkan |
| 2002/0183817 A1 | 12/2002 | Van Venrooij et al. |
| 2003/0163171 A1 | 8/2003 | Kast et al. |
| 2004/0064164 A1 | 4/2004 | Ries et al. |
| 2004/0230268 A1 | 11/2004 | Huff et al. |
| 2004/0260373 A1 | 12/2004 | Ries et al. |

(56) References Cited

U.S. PATENT DOCUMENTS

| | | |
|---|---|---|
| 2005/0015130 A1 | 1/2005 | Gill |
| 2005/0027326 A1 | 2/2005 | Ries et al. |
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1 | 2/2005 | Sommer et al. |
| 2005/0137665 A1 | 6/2005 | Cole |
| 2005/0171587 A1 | 8/2005 | Daglow et al. |
| 2005/0186829 A1 | 8/2005 | Balsells |
| 2005/0272280 A1 | 12/2005 | Osypka |
| 2006/0015163 A1 | 1/2006 | Brown |
| 2006/0025841 A1 | 2/2006 | McIntyre |
| 2006/0030918 A1 | 2/2006 | Chinn |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholdt et al. |
| 2007/0042648 A1 | 2/2007 | Balsells |
| 2007/0142889 A1 | 6/2007 | Whitehurst et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Boyd et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0264943 A1 | 10/2009 | Barker |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0022100 A1 | 1/2011 | Brase et al. |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 | 11/2011 | Janzig et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0053646 A1 | 3/2012 | Brase et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0185019 A1 | 7/2012 | Schramm et al. |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0025609 A1 | 1/2015 | Govea |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0158558 A1 | 6/2016 | Shanahan et al. |
| 2016/0206891 A1 | 7/2016 | Howard et al. |
| 2016/0228692 A1 | 8/2016 | Steinke et al. |
| 2016/0296745 A1 | 10/2016 | Govea et al. |
| 2016/0375238 A1 | 12/2016 | Leven et al. |
| 2017/0072187 A1 | 3/2017 | Howard et al. |
| 2017/0143978 A1 | 5/2017 | Barker |
| 2017/0203104 A1 | 7/2017 | Nageri et al. |
| 2017/0333702 A1* | 11/2017 | Barner ............... A61N 1/0558 |
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0243570 A1 | 8/2018 | Malinowski et al. |
| 2018/0289968 A1 | 10/2018 | Lopez |
| 2018/0369596 A1 | 12/2018 | Funderburk |
| 2019/0030345 A1 | 1/2019 | Funderburk |
| 2019/0103696 A1 | 4/2019 | Conger |

FOREIGN PATENT DOCUMENTS

| | | |
|---|---|---|
| EP | 0832667 B1 | 2/2004 |
| EP | 1181947 B1 | 1/2006 |
| EP | 1625875 | 2/2006 |
| EP | 2092952 A1 | 8/2009 |
| WO | 1997032628 A1 | 9/1997 |

(56) References Cited

FOREIGN PATENT DOCUMENTS

| | | |
|---|---|---|
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

\* cited by examiner

CONNECTOR ASSEMBLIES WITH NOVEL SPACERS FOR ELECTRICAL STIMULATION SYSTEMS AND METHODS OF MAKING AND USING SAME

CROSS-REFERENCE TO RELATED APPLICATIONS

This application claims the benefit under 35 U.S.C. § 119(e) of U.S. Provisional Patent Application Ser. No. 62/617,990, filed Jan. 16, 2018, which is incorporated herein by reference.

FIELD

The present invention is directed to the area of implantable electrical stimulation systems and methods of making and using the systems. The present invention is also directed to connectors utilizing a novel spacer design, as well as methods of making and using the same.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a connector assembly including an elongated connector housing having a first end, a second end, and a length, the connector housing defining a port at the second end of the connector housing, the port configured for receiving a proximal end of a lead or lead extension; a lead lumen that extends from the port along at least a portion of the length of the connector housing; connector contacts axially spaced-apart and disposed along the lead lumen such that the connector contacts are each exposed to the lead lumen, the connector contacts configured for coupling to terminals along a proximal end of a lead or lead extension when the proximal end of the lead or lead extension is inserted into the lead lumen; and non-conductive spacers disposed between adjacent connector contacts. Each of the spacers includes a first radial sidewall, a second radial sidewall, and an intermediate region extending between, and connecting, the first and second radial sidewalls. The first and second radial sidewalls and intermediate region define boundaries of an open circumferential space. wherein the first and second radial sidewalls and intermediate region define boundaries of an open circumferential space. The open circumferential space is disposed on a first side of the intermediate region and the lead lumen is disposed on a second side of the intermediate region opposite the first side. The intermediate region is configured and arranged to form a seal with the proximal end of the lead or lead extension when inserted into the lead lumen.

In at least some embodiments, the first and second radial sidewalls and the intermediate region, in combination, have a U-shaped cross-section. In at least some embodiments, the intermediate region has a V-shaped cross-section. In at least some embodiments, in cross-section, the intermediate region is curved towards a center of the lead lumen. In at least some embodiments, in cross-section, the intermediate region forms right angles with the first and second sidewalls.

In at least some embodiments, the spacer further includes a bridge extending from the first radial sidewall to the second radial sidewall and forming an additional boundary of the open circumferential space. In at least some embodiments, the spacer further includes a radial ridge extending inwardly from surface of the intermediate region and around at least a portion of a perimeter of the surface of the intermediate region. In at least some embodiments, the radial ridge extends around the entire perimeter of the surface of the intermediate region.

In at least some embodiments, the intermediate region is configured and arranged to stretch or deflect when the proximal end of the lead or lead extension is inserted into the lead lumen. In at least some embodiments, the first radial sidewall, second radial sidewall, and intermediate region have an equal thickness when a lead or lead extension is not inserted into the lead lumen. In at least some embodiments, the connector assembly is configured and arranged so that at least one of the connector contacts acts as a stop to stretching or deflection of the intermediate region of at least one of the spacers as the proximal end of the lead or lead extension is inserted into the lead lumen. In at least some embodiments, the connector assembly is configured and arranged so that at least one of the connector contacts acts as a stop to retraction of the intermediate region of at least one of the spacers as the proximal end of the lead or lead extension is removed into the lead lumen.

In at least some embodiments, at least one of the first and second radial sidewalls is configured and arranged to form a seal with the connector housing. In at least some embodiments, the first radial sidewall is configured and arranged to stretch or deflect when the proximal end of the lead or lead extension is inserted into the lead lumen. In at least some embodiments, the second radial sidewall is configured and arranged to stretch or deflect when the proximal end of the lead or lead extension is inserted into the lead lumen.

Another embodiment is an electrical stimulating system including an electrical stimulation lead including a proximal end, a distal end, a plurality of terminals disposed along the proximal end, and a plurality of electrodes disposed along the distal end; and a control module coupleable to the electrical stimulation lead. The control module includes a housing, an electronic subassembly disposed in the housing; and any of the connector assemblies describe above, where at least one of the connector contacts is electrically coupled to the electronic subassembly.

Yet another embodiment is a lead extension including any of the connector assemblies describe above disposed on a first end of the lead extension; and terminals disposed along a second end of the lead extension. A further embodiment is a lead assembly that includes the lead extension and a lead. Another embodiment is an electrical stimulation system that includes the lead assembly and a control module coupleable to the lead assembly. The control module includes a housing and an electronic subassembly disposed in the housing. In at least some embodiments, the control module also includes any of the connector assemblies described above.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to connectors utilizing a novel spacer design, as well as methods of making and using the same.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Examples of connectors, connector contacts and connector assemblies for electrical stimulation systems with leads are found in, for example, U.S. Pat. Nos. 8,849,396; 7,244,150; 8,600,507; 8,897,876; 8,682,439; U.S. Patent Applications Publication Nos. 2012/0053646; 2014/0148885; 2015/0209575; 2016/0059019; and U.S. Patent Provisional Patent Application Nos. 62/193,472; 62/216,594; 62/259,463; and 62/278,667, all of which are incorporated by reference in their entireties.

Figure 1:
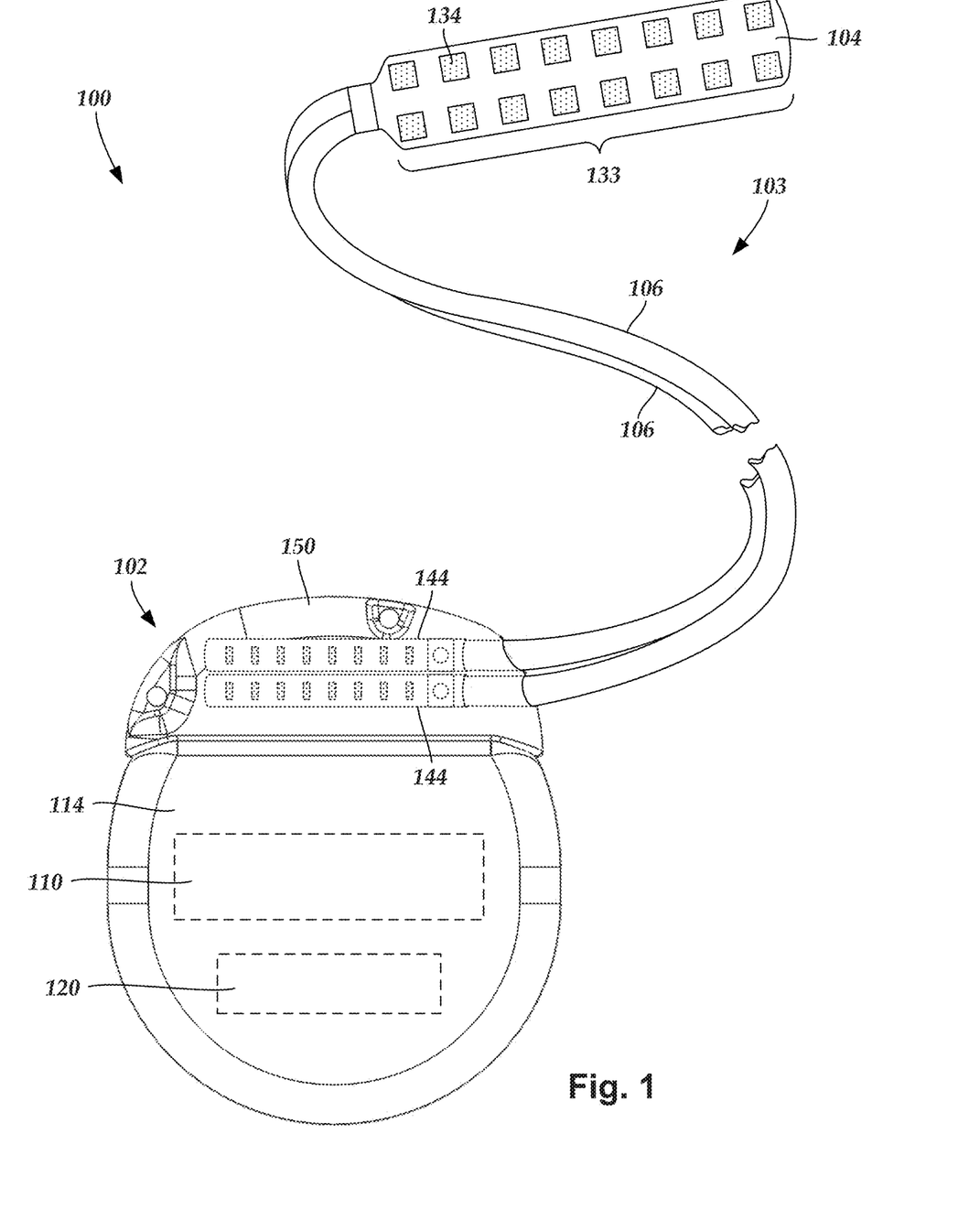
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
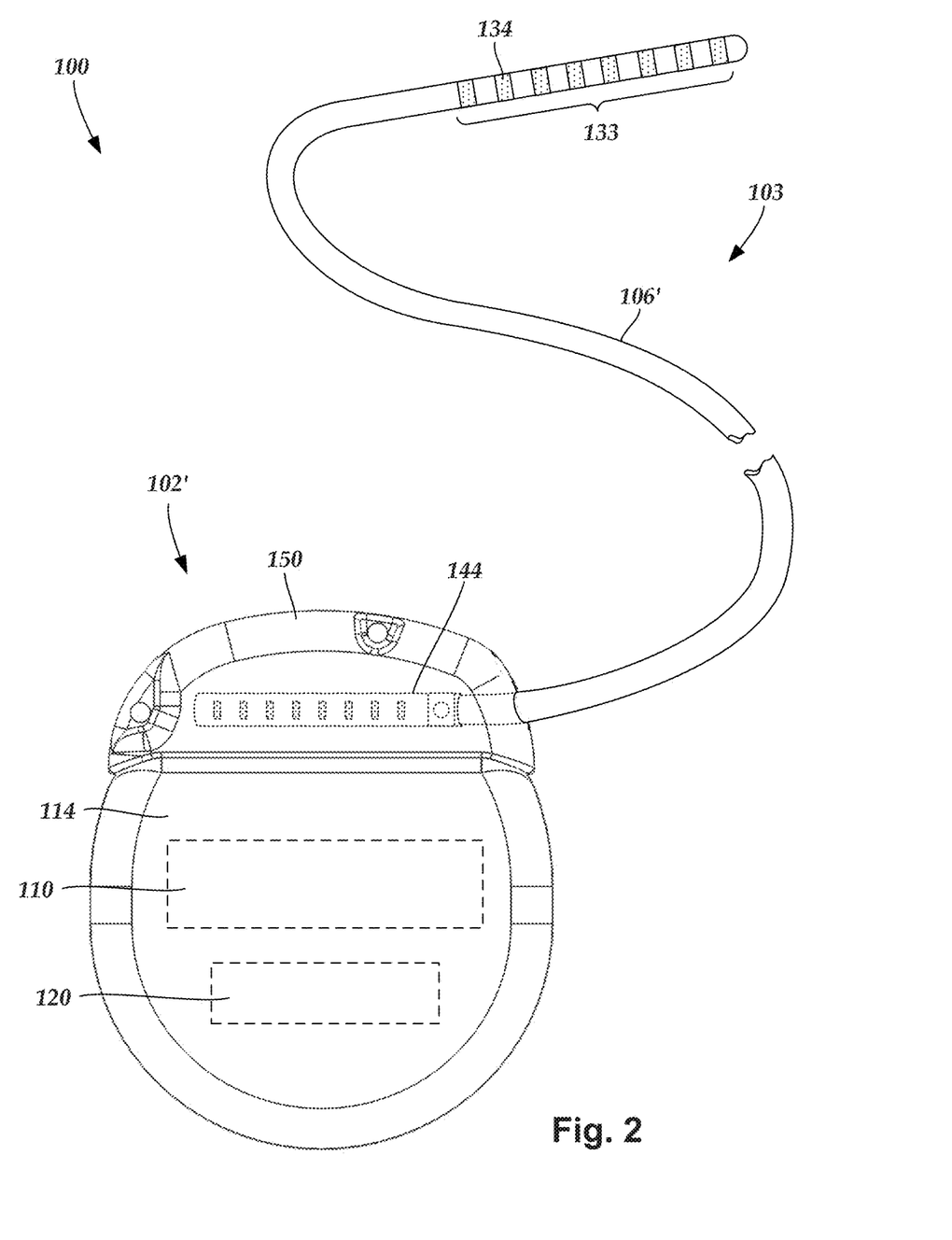
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
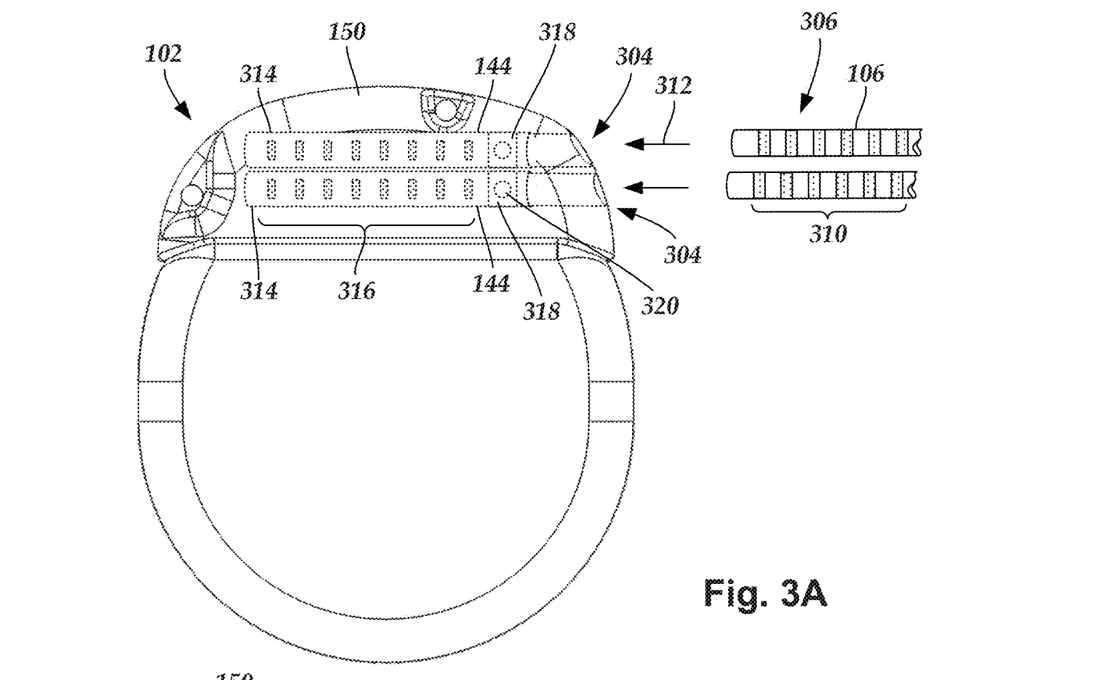
FIG. 3A is a schematic view of one embodiment of a plurality of connector assemblies disposed in the control module of FIG. 1, the connector assemblies configured to receive the proximal portions of the lead bodies of FIG. 1, according to the invention.
Figure 3B:
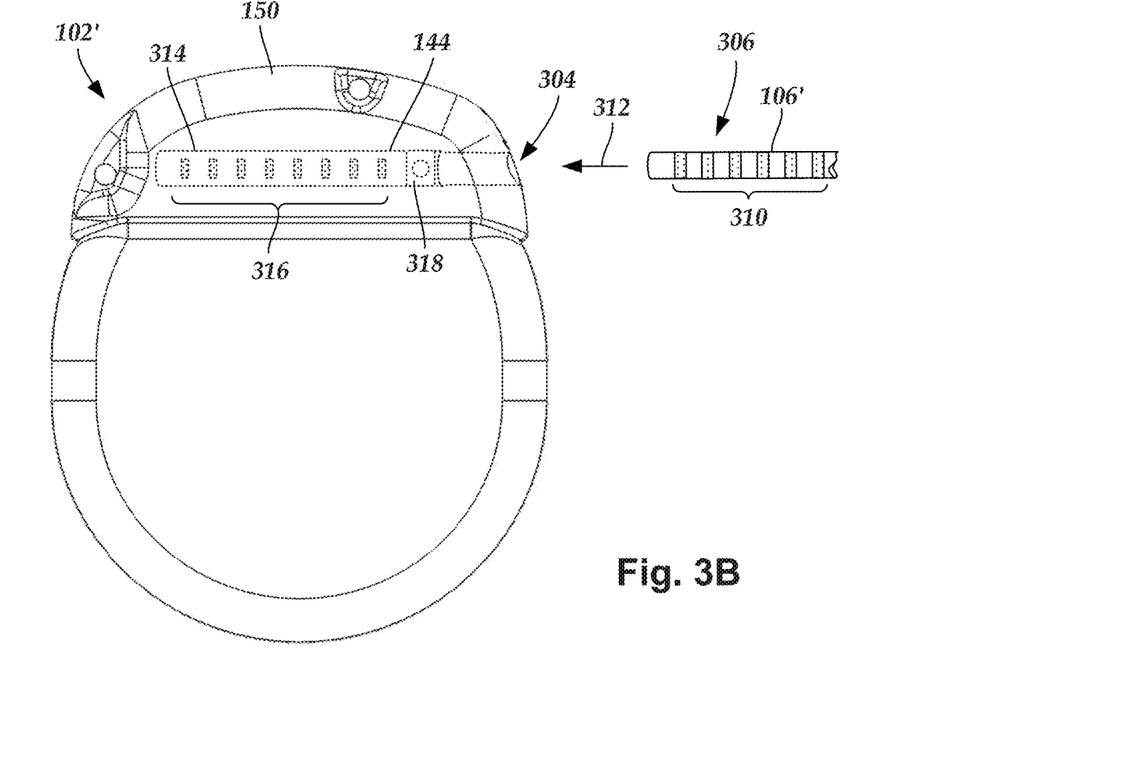
FIG. 3B is a schematic view of one embodiment of a connector assembly disposed in the control module of FIG. 2, the connector assembly configured to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured for insertion to the control module 102. FIG. 3B is a schematic side view of one embodiment of a single connector assembly 144 disposed on the control module 102'. In FIG. 3B, the proximal end 306 of the single lead body 106' is shown configured for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
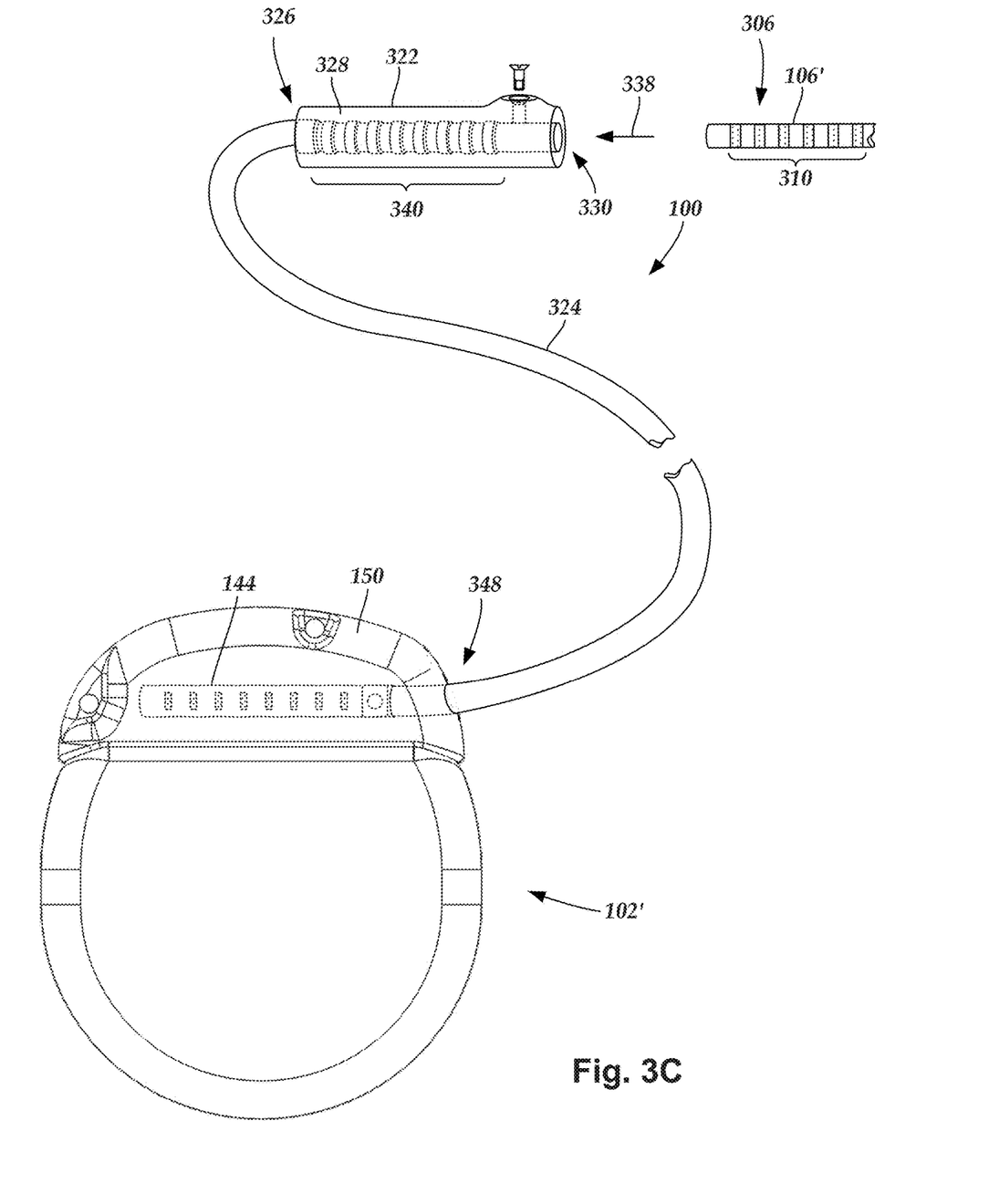
FIG. 3C is a schematic view of one embodiment of a proximal portion of the lead body of FIG. 2, a lead extension, and the control module of FIG. 2, the lead extension configured to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured for insertion into a lead extension connector assembly disposed in another lead extension. In other embodiments (as shown in FIG. 3C), the proximal end 348 of the lead extension 324 is configured for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

It will be understood that the connector assembly described below may be disposed in many different locations including, for example, on lead extensions (see e.g., 322 of FIG. 3C), lead adapters, lead splitters, the connector portion of control modules (see e.g., 144 of FIGS. 1-3B), or the like. In preferred embodiments, the connector assemblies are disposed on the distal ends of lead extensions.

A connector assembly in the control module or on a lead extension or other location can include an arrangement of connector contacts separated by spacers (which may also be referred to as seals). The spacers isolate or electrically insulate the connector contacts from each other and may also provide a seal with the lead to further isolate the connector contacts from each other. The spacers provide a sealing force or pressure on the lead body and array of terminals at an end of the lead or lead extension. Providing the seal increases the force for insertion of the lead or lead extension. The insertion force may result in difficulty inserting a lead, user dissatisfaction, or even lead damage due to high columnar loads. Moreover, as the number of electrodes on a lead increases, adding more connector contacts in a connector and terminals on the lead or lead extension will typically increase the insertion force. Therefore, it is desirable to develop spacer configurations with lower insertion force than conventional spacers.

A spacer can include radial sidewalls with an intermediate region extending between, and connecting, the radial sidewalls. The radial sidewalls and intermediate region define (e.g., form at least a portion of a boundary for) an open circumferential space opposite the lead lumen of the connector to facilitate stretching, deflection, or other deformation of the spacer as the lead is inserted or removed from the connector. In at least some embodiments, the open circumferential space is disposed on a first side of the intermediate region and the lead lumen is disposed on a second side of the intermediate region opposite the first side. In at least some embodiments, this spacer can provide a reliable seal with the lead or lead extension inserted into the connector and may also provide a seal with a housing of the connector.

Figure 4:
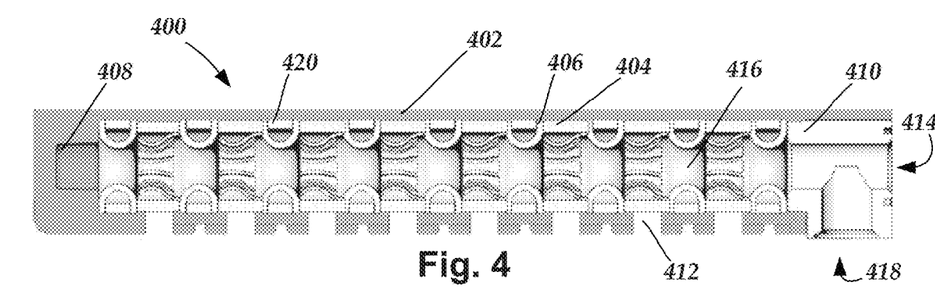
FIG. 4 is a schematic, cross-sectional view of one embodiment of a connector assembly according to the invention.

FIG. 4A shows a schematic, perspective view of a connector assembly 400 having a connector housing 402, connector contacts 404, spacers 406 that separate the connector contacts, an optional end stop 408, and an optional retention block 410. The connector housing 402 includes apertures 412 exposing the individual connector contacts 404 for attachment of a conductor (e.g., a wire—not shown) to the connector contact. In at least some embodiments, the apertures 412 in a finished connector assembly 400 are filled after or during attachment of the conductors to the connector contacts 404. Optionally, the connector assembly 400 includes, for one or more (or all) of the spacers 406, a support ring 420 as part of the corresponding spacer or as a separate component.

The connector housing 402 defines a port 414 that provides access to a lead lumen 416 and the connector contacts 404. The connector housing 402 can be made of any suitable material or materials. In at least some embodiments, the connector assembly 400 further includes a retention block 410 to fasten the corresponding lead body (or a retention ring on the lead body) of the lead or lead extension to the connector assembly 400 when the lead body is inserted into the connector assembly and prevent undesired detachment of the lead body from the connector assembly or misalignment of the terminals on the lead body with the connector contacts. For example, the retaining element 318 may include an aperture 418 through which a fastener (e.g., a set screw, pin, or the like) may be inserted and secured against an inserted lead body. Other types of retention blocks or retention assemblies can be used including, but not limited to, those described in U.S. Pat. No. 9,440,066; U.S. patent application Ser. Nos. 15/627,016 and 15/641,688; and U.S. Provisional Patent Application Ser. No. 62/464,710, all of which are incorporated herein by reference.

The connector contacts 404 may take the form of conductive spring contacts or any other suitable contact arrangement. Examples of connector contacts include, but are not limited to, canted coil contacts available from Bal Seal Engineering, Inc. (Foothill Ranch, Calif.) and contacts described in U.S. Pat. Nos. 7,803,021; 8,682,439; 8,897,876; 9,409,032; 9,604,068; 9,656,093; and 9,770,598; U.S. Patent Application Publications Nos. 2011/0022100; 2016/0228692; and 2016/0296745; U.S. patent application Ser.

Nos. 15/627,016 and 15/656,612; and U.S. Provisional Patent Application Ser. No. 62/483,141, all of which are incorporated herein by reference.

The connector assembly 400 may include an end stop 408 which, at least in part, modulates insertion of the lead or lead extension into the port 414. The end stop 408 can be disposed in the lead lumen 416 of the connector assembly 400. The end stop 408 can provide one or more surfaces upon which the inserted lead or lead extension contacts, when the lead or lead extension is fully inserted into the port 414. In some cases, the end stop 408 can provide the proximal-most point of insertion for the lead or lead extension within the connector assembly 400.

Figure 5A:
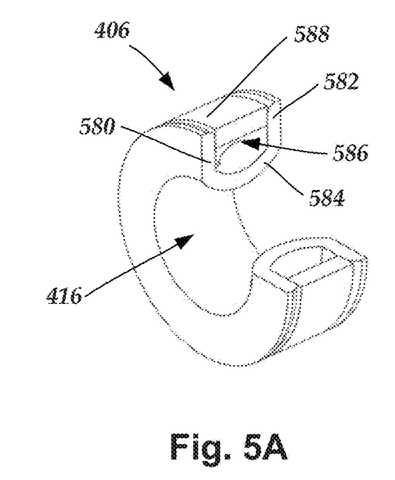
FIG. 5A is a schematic, partially cut away, perspective view of one embodiment of a spacer, according to the invention.
Figure 5B:
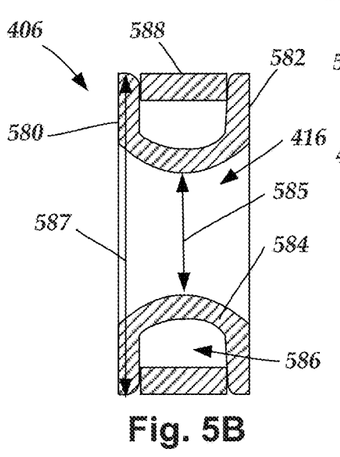
FIG. 5B is a schematic, cross-sectional view of the spacer of FIG. 5A, according to the invention.

FIGS. 5A and 5B illustrate schematic views (perspective view—FIG. 5A and cross-sectional view—FIG. 5B) of one embodiment of a spacer 406. The spacer 406 can be described as having a first radial sidewall 580, a second radial sidewall 582, and an intermediate region 584 that extends between, and connects, the first and second radial sidewalls. In the illustrated embodiment of FIGS. 5A and 5B, the first radial sidewall 580, the second radial sidewall 882, and the intermediate region 584, in combination, are U-shaped in cross-section. The intermediate region 584 of the illustrated embodiment in FIGS. 5A and 5B is curved towards the center of the lead lumen 416.

The first and second radial sidewalls 580, 582 and intermediate region 584 define, at least in part, an open circumferential space 586. The open circumferential space 586 is opposite the lead lumen 416 with respect to the intermediate region 584. The first and second radial sidewalls 580, 582 and the intermediate region 584 can form, at least in part, boundaries of the open circumferential space 586. The open circumferential space 586. The open circumferential space 586 separates the first radial sidewall 580 from the second radial sidewall 582. In at least some embodiments, the presence of the open circumferential space 586 facilitates deformation of the first radial sidewall 580, second radial sidewall 582, or intermediate region 584 (or any combination thereof) during insertion or removal of the lead from the lead lumen 416 (see, for example, FIGS. 6A-6F). For example, in at least some embodiments, the open circumferential space 586 does not impede the deformation of the spacer 406.

Optionally, the spacer 406 can include a bridge 588 that connects the first radial sidewall 580 to the second radial sidewall 582 along an outer portion of the spacer 406. The bridge 588 may further define the open circumferential space 586. The bridge 588 may provide additional stability to the spacer 406 and prevent or reduce longitudinal compression of the sidewalls 580, 582 towards each other.

The spacer 406 can be made of any suitable flexible, non-conductive material including, but not limited to, silicone, polyurethane, or the like. The material of the spacer 406 is preferably stretchable. In at least some embodiments, the spacer 406 is formed by molding.

The shortest inner diameter 585 of the intermediate region 584 is preferably equal to, or slightly smaller (for example, no more than 15%, 10%, or 5% smaller) than, the diameter of the lead or lead extension to be inserted into the connector assembly 400. In at least some embodiments, the intermediate region 584 makes a seal (preferably, a hermetic seal) with the portion of the lead or lead extension inserted into the connector assembly 400. In at least some embodiments, a ratio of sealing force to insertion force is at least 1.5, 1.6, 1.7, or 1.8. This ratio can be determined using a finite element analysis.

Although not wishing to be bound to any particular theory, the following is a description of one method of analyzing the sealing force and the insertion force. In at least some embodiments, the insertion force can be considered the combination of two forces: displacement and friction. Displacement is the force generated by moving the portions of the spacer 406, such as, but not limited to, the intermediate region 584. As one example of a determination of the displacement force, when the spacer 406 is deformed (see, for example, FIGS. 6A-6F), the displacement force is proportional to the product of the displacement, the elastic modulus, and the second polar moment of inertia divided by the length of the bending element (e.g., $F_{dis}=d*E*I/L$). In at least some embodiments, when the material of the spacer 406 is stretched (see, for example, FIG. 6B), the displacement can be modeled using Hook's law with the force equal to the product of the stretching distance and a material constant, k, (e.g., $F=kx$). In at least some embodiments, friction is equal to the product of the normal force and a friction coefficient, $\mu$ (e.g., $F=\mu N$). In at least some embodiments, the normal force is the sealing force and may be, for example, derived from the radial component of a force related to the stretching of the spacer 406. The friction coefficient depends on the materials of the spacer and the lead, in combination, and other factors such surface texture and possibly lubricity. Calculation of these forces in 360 degrees with multiple interactions between these forces can be complicated, but may be modeled.

In at least some embodiments, the outer diameter 587 of the spacer 406 is equal to or slightly larger (for example, no more than 15%, 10%, or 5% larger) than, the inner diameter of the connector housing 402 of the connector assembly 400. In at least some embodiments, the first radial sidewall or second radial sidewall 580, 582 (or both) makes a seal (preferably, a hermetic seal) with the connector housing 402 of the connector assembly 400. In at least some embodiments, the first radial sidewall and second radial sidewall 580, 582 make a seal (preferably, a hermetic seal) with the adjacent connector contacts 404 (or with an adjacent connector contact 404 and the end stop 408 or retention block 410) of the connector assembly 400.

In at least some embodiments, the thicknesses of the first radial sidewall 580, the second radial sidewall, and the intermediate region 584 are equal or differ by no more than 5%, 10%, or 20%. In other embodiments, the first and second radial sidewalls 580, 582 can be thicker or thinner than the intermediate region 584. In at least some embodiments, the thicknesses of the first and second radial sidewalls may be different from each other. In at least some embodiments, the thicknesses of the first radial sidewall 580, the second radial sidewall, and the intermediate region 584 may vary.

Figure 5C:
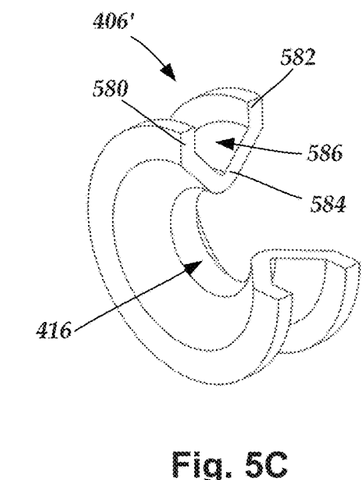
FIG. 5C is a schematic, partially cut away, perspective view of a second embodiment of a spacer, according to the invention.
Figures 5D, 5E:
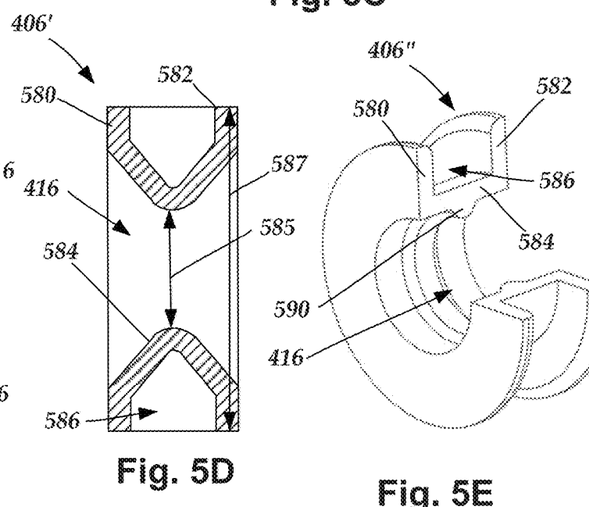
FIG. 5D is a schematic, cross-sectional view of the spacer of FIG. 5C, according to the invention.
FIG. 5E is a schematic, cross-sectional view of a third embodiment of a spacer, according to the invention.

FIGS. 5C and 5D illustrate a second embodiment of a spacer 406' and FIG. 5E illustrates a third embodiment of a spacer 406". The spacers 406', 406" both include a first radial sidewall 580, second radial sidewall 582, and an intermediate region 584 and the arrangement, design considerations, features, and properties of these spacers and their component elements are the same as, unless indicated otherwise, the elements described above with respect to spacer 406 illustrated in FIGS. 5A and 5B.

The intermediate region 584 of the spacer 406' of FIGS. 5C and 5D has a V-shape in cross-section. The intermediate region 584 of the spacer 406" of FIG. 5E is, in cross-section, straight between the two radial sidewalls 580, 582 and forms a right angle with the first and second radial sidewalls 580, 582. The intermediate region 584, first radial sidewall 580, and second radial sidewall 582 of spacer 406" in FIG. 5E may be considered as forming a "square U" in cross-section.

Any of the embodiments described herein can include one or more radial ridges 590 (FIG. 5E) extending around a portion of (or the entire) perimeter of the lead-contacting surface of the intermediate region 584, as illustrated in FIG. 5E. The illustrated embodiment in FIG. 5E has one radial ridge that is centered on the intermediate region 584 and extends around the entire perimeter of the lead-contacting surface of the intermediate region. It will be recognized that any other number of radial ridges (e.g., two, three, four, or more) can be used and that the radial ridges may only extend around a portion of the perimeter or may be separated into multiple segments (for example, two, three, four, or more segments) that each extend around only a portion of the perimeter. Moreover, the radial ridge(s) 590 need not be centered with respect to the intermediate region 584 but can be spaced apart from either side of the center. The radial ridge(s) 590 may facilitate forming a seal with the lead or lead extension.

FIGS. 6A-6F are cross-sectional views of a portion of a spacer 406' (see, FIGS. 5C and 5D), lead 106, and contact 404 during the insertion (FIGS. 6A-6C) and retraction (FIGS. 6D-6F) of the lead 106 into/out of a connector assembly. These FIGS. 6A-6F illustrate one embodiment of the alterations to the spacer 406' during the insertion/retraction processes. It will be recognized that other spacers of the invention made of different materials or having different forms may move, stretch, deflect, or otherwise deform differently.

Figure 6A:
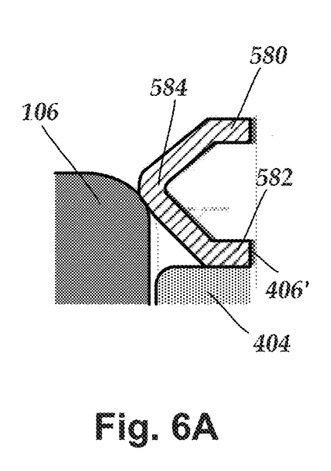
FIGS. 6A-6F are a schematic, cross-sectional views of a portion of the spacer of FIG. 5C, a connector contact, and a lead illustrating one embodiment of interaction between the spacer and the lead during insertion and retraction of the lead from a connector assembly, according to the invention.
Figure 6B:
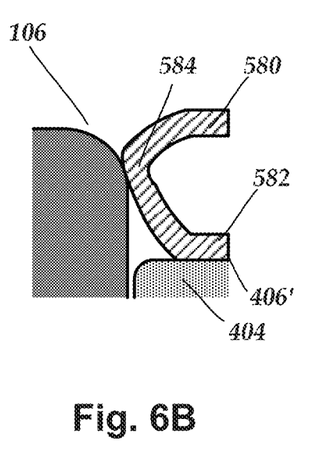
Figure 6C:
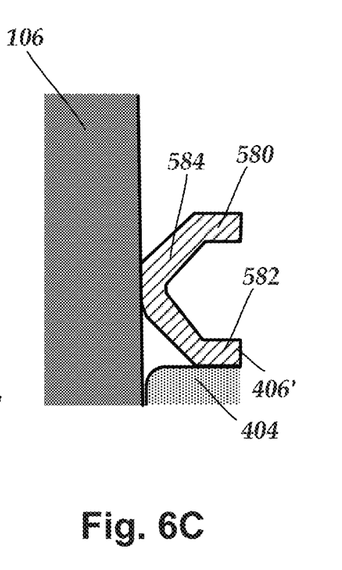

In FIG. 6A, the end of the lead 106 makes contact with the spacer 406'. As the lead 106 is pushed past the spacer 406', the intermediate region 584 of the spacer may stretch, deflect, or deform, as illustrated in FIG. 6B. In some instances, one or both of the first radial sidewall 580 or second radial sidewall 582 may also deform, deflect, or stretch. As the lead 106 is fully inserted into the connector assembly, the intermediate region 584 may return to its original shape or a form similar to its original shape, as illustrated in FIG. 5C. In other embodiments, the intermediate region may remain substantially stretched, deflected, or otherwise deformed. In some embodiments, an adjacent connector contact 404 (FIG. 4) or end stop 408 (FIG. 4) may prevent or reduce further stretching or deflection of the intermediate region 584. Preferably, the intermediate region 584 makes a seal (more preferably, a hermetic seal) with the lead 106.

Figure 6D:
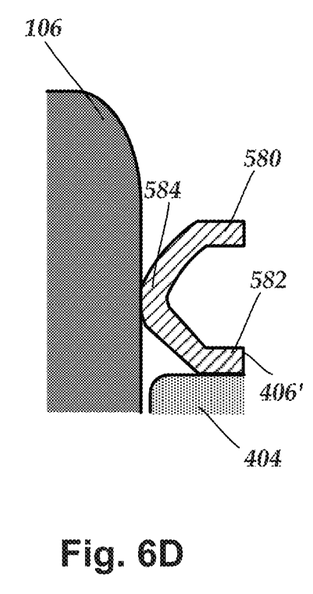
Figure 6E:
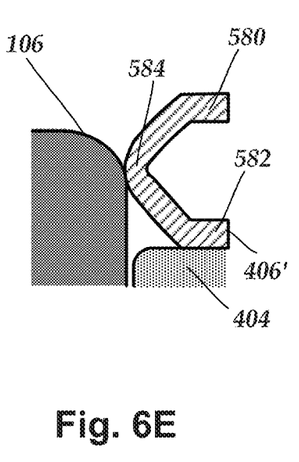
Figure 6F:
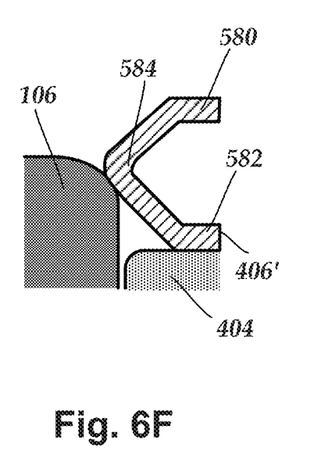

As the lead is retracted, the intermediate region 584 moves back toward the connector contact 404, as illustrated in FIGS. 6D and 6E, and may stretch, deflect, or otherwise deform. In at least some embodiments, the connector contact 404 may prevent or hinder the intermediate region 584 from rolling backward and inverting. As the end of the lead 106 moves past spacer 406', the intermediate region 584 may return to its original shape, as illustrated in FIG. 6F, (although, in some embodiments, there may be residual deformation, deflection, stretching, or other inelastic changes to the spacer shape).

Figure 7:
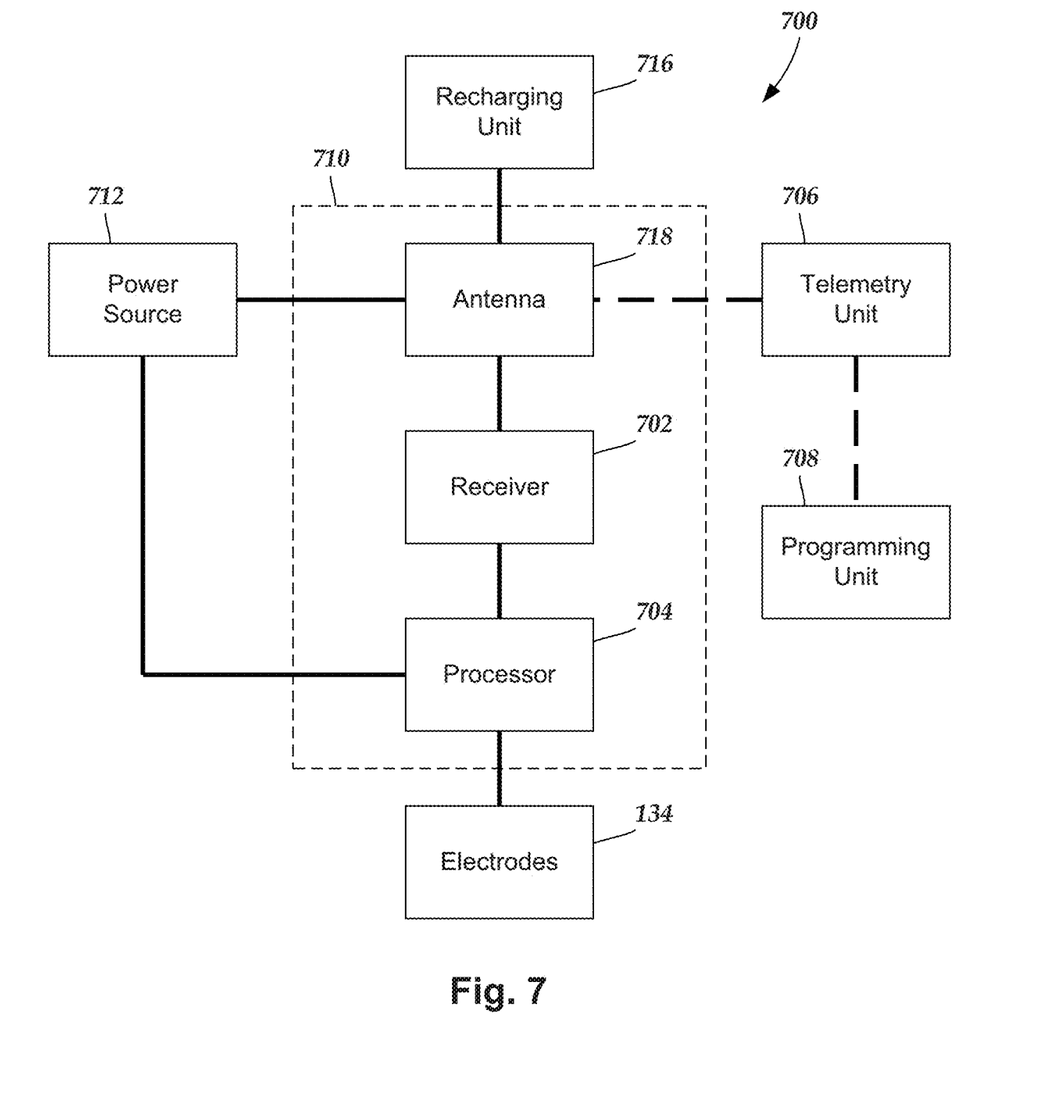
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 selects which electrode(s) are cathodes and which electrode(s) are anodes. In some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A connector assembly, comprising:
   an elongated connector housing having a first end, a second end, and a length, the connector housing defining a port at the second end of the connector housing, the port configured for receiving a proximal end of a lead or lead extension;
   a lead lumen that extends from the port along at least a portion of the length of the connector housing;
   a plurality of connector contacts axially spaced-apart and disposed along the lead lumen such that the connector contacts are each exposed to the lead lumen, the connector contacts configured for coupling to terminals along the proximal end of the lead or lead extension when the proximal end of the lead or lead extension is inserted into the lead lumen; and
   a plurality of non-conductive spacers disposed between adjacent connector contacts, each of the spacers comprising a first radial sidewall, a second radial sidewall, and an intermediate region extending between, and connecting, the first and second radial sidewalls, wherein the first and second radial sidewalls and intermediate region define boundaries of an open circumferential space, wherein the open circumferential space is disposed on a first side of the intermediate region and the lead lumen is disposed on a second side of the intermediate region opposite the first side, wherein the intermediate region is configured and arranged to form a seal with the proximal end of the lead or lead extension when inserted into the lead lumen.

2. The connector assembly of claim 1, wherein the first and second radial sidewalls and the intermediate region, in combination, have a U-shaped cross-section.

3. The connector assembly of claim 1, wherein the intermediate region has a V-shaped cross-section.

4. The connector assembly of claim 1, wherein, in cross-section, the intermediate region is curved towards a center of the lead lumen.

5. The connector assembly of claim 1, wherein, in cross-section, the intermediate region forms right angles with the first and second sidewalls.

6. The connector assembly of claim 1, wherein the spacer further comprises a bridge extending from the first radial sidewall to the second radial sidewall and forming an additional boundary of the open circumferential space.

7. The connector assembly of claim 1, wherein the spacer further comprises a radial ridge extending inwardly from a surface of the intermediate region and around at least a portion of a perimeter of the surface of the intermediate region.

8. The connector assembly of claim 7, wherein the radial ridge extends around the entire perimeter of the surface of the intermediate region.

9. The connector assembly of claim 1, wherein the intermediate region is configured and arranged to stretch or deflect when the proximal end of the lead or lead extension is inserted into the lead lumen.

10. The connector assembly of claim 1, wherein the first radial sidewall, second radial sidewall, and intermediate region have an equal thickness when a lead or lead extension is not inserted into the lead lumen.

11. The connector assembly of claim 1, wherein the connector assembly is configured and arranged so that at least one of the connector contacts acts as a stop to stretching or deflection of the intermediate region of at least one of the spacers as the proximal end of the lead or lead extension is inserted into the lead lumen.

12. The connector assembly of claim 1, wherein the connector assembly is configured and arranged so that at least one of the connector contacts acts as a stop to retraction of the intermediate region of at least one of the spacers as the proximal end of the lead or lead extension is removed into the lead lumen.

13. The connector assembly of claim 1, wherein at least one of the first and second radial sidewalls is configured and arranged to form a seal with the connector housing.

14. The connector assembly of claim 1, wherein the first radial sidewall is configured and arranged to stretch or deflect when the proximal end of the lead or lead extension is inserted into the lead lumen.

15. The connector assembly of claim 14, wherein the second radial sidewall is configured and arranged to stretch or deflect when the proximal end of the lead or lead extension is inserted into the lead lumen.

16. An electrical stimulating system comprising:
   an electrical stimulation lead comprising a proximal end, a distal end, a plurality of terminals disposed along the proximal end, and a plurality of electrodes disposed along the distal end; and
   a control module coupleable to the electrical stimulation lead, the control module comprising
      a housing,
      an electronic subassembly disposed in the housing; and
      the connector assembly of claim 1, wherein at least one of the connector contacts is electrically coupled to the electronic subassembly.

17. A lead extension, comprising
   the connector assembly of claim 1 disposed on a first end of the lead extension; and a plurality of terminals disposed along a second end of the lead extension.

18. A lead assembly, comprising:
a lead; and
the lead extension of claim 17.

19. An electrical stimulation system, comprising:
the lead assembly of claim 18; and
a control module coupleable to the lead assembly, the control module comprising
a housing, and
an electronic subassembly disposed in the housing.

20. An electrical stimulation system, comprising:
a lead; and
a lead extension coupleable to the lead; and
a control module coupleable to the lead extension, the control module comprising
a housing, and
an electronic subassembly disposed in the housing;
wherein the lead extension and the control module each individually comprise the connector assembly of claim 1.

* * * * *